US012611332B2

(12) United States Patent

Huh et al.

(10) Patent No.: US 12,611,332 B2

(45) Date of Patent: Apr. 28, 2026

(54) WELDING INFORMATION PROVIDING APPARATUS

(71) Applicant: OTOS WING CO.,LTD., Seoul (KR)

(72) Inventors: Moon Young Huh, Seoul (KR); Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 91 days.

(21) Appl. No.: 18/605,824

(22) Filed: Mar. 15, 2024

(65) Prior Publication Data

US 2024/0307230 A1     Sep. 19, 2024

(30) Foreign Application Priority Data

Mar. 16, 2023     (KR) ........................ 10-2023-0034634

(51) Int. Cl.
| | |
|---|---|
| *A61F 9/06* | (2006.01) |
| *B23K 31/12* | (2006.01) |
| *G02B 27/01* | (2006.01) |
| *G03B 13/36* | (2021.01) |

(52) U.S. Cl.
CPC ................ *A61F 9/06* (2013.01); *B23K 31/12* (2013.01); *G02B 27/0101* (2013.01); *G03B 13/36* (2013.01); *G02B 2027/0138* (2013.01)

(58) Field of Classification Search
CPC ........... A61F 9/06; B23K 31/12; B23K 37/00; B23K 37/006; G02B 27/0101; G02B 2027/0138; G02B 26/0883; G03B 13/36; G03B 13/32; F16P 1/06; G01J 1/02; H04N 7/18; H04N 23/54; H04N 23/55
See application file for complete search history.

(56) References Cited

U.S. PATENT DOCUMENTS

| | | | | |
|---|---|---|---|---|
| 10,701,270 | B1 * | 6/2020 | LaFlech | H04N 23/63 |
| 2011/0024402 | A1 * | 2/2011 | Hozumi | B23K 26/14 |
| | | | | 219/121.64 |
| 2015/0320601 | A1 * | 11/2015 | Gregg | G06T 1/0007 |
| | | | | 2/8.2 |
| 2016/0175964 | A1 * | 6/2016 | Penoyer | B23K 9/0956 |
| | | | | 219/137 R |
| 2018/0301056 | A1 * | 10/2018 | Cross | H04N 21/41407 |
| 2021/0085524 | A1 * | 3/2021 | Huh | A61F 9/067 |
| 2023/0053923 | A1 | 2/2023 | Huh | |

FOREIGN PATENT DOCUMENTS

| | | |
|---|---|---|
| KR | 10-2018-0102418 | 9/2018 |
| KR | 10-2022-0023272 | 3/2022 |

* cited by examiner

*Primary Examiner* — Shahan Ur Rahaman
(74) *Attorney, Agent, or Firm* — PnK IP LLC

(57)     ABSTRACT

Provided is a welding information providing apparatus including a main body provided to be worn by a user, a camera unit including at least one camera attached to an outer side of the main body and obtaining welding image frames with respect to a welding operation, a display unit disposed inside the main body and providing a welding image to the user, and a processor configured to control the display unit to display the welding image generated based on the welding image frames, wherein the camera unit obtains the welding image frame by setting or disabling an auto-focus (AF) function according to an input of the user or pre-set conditions.

17 Claims, 8 Drawing Sheets

1100                 1200

WELDING INFORMATION PROVIDING APPARATUS

CROSS-REFERENCE TO RELATED APPLICATION

This application claims priority from and the benefit of Korean Patent Application No. 10-2023-0034634, filed on Mar. 16, 2023, which is hereby incorporated by reference for all purposes as if fully set forth herein.

BACKGROUND

Field

One or more embodiments of the disclosure relate to a welding information providing apparatus.

Discussion of the Background

A user wears a protector for protection from light and high temperature heat generated during a welding process. The user may check only the progress of welding through the protective gear while wearing the protective gear, and thus needs to remove the protective gear and check with the naked eye to check various types of information for welding, such as conditions set in a welding device.

When the skill level of the user is not high, in particular, when wearing an automatic welding mask or a manual welding mask, the user may see only a portion adjacent to welding light and may not easily recognize a detailed welding situation such as a welding surrounding environment. Accordingly, it is necessary to provide the user with a high-definition image that allows the user to visually check the welding surroundings, and provide the user with specific information about welding status information.

Moreover, illuminance/luminance of a welding light spot are very high during the welding operation, a darkening filter is used to protect eyes of the user from the welding light spot and to allow the welding operation to be performed effectively. In this case, other region than the welding light spot is not visible at all, which makes the welding operation difficult and degrades accuracy in the welding.

On the other hand, when a welding image is obtained by using a camera and provided to a user, the camera's auto-focus function causes an image to shake or delayed during the focusing process, and thus accurate images may not be provided in real time. As a result, smooth work may be interfered and a user may be unable to quickly respond to dangerous situations.

The above issue may identically occur for medical staff during skin treatment and/or diagnosis performed by using high-luminance/high-illuminance light such as laser light, as well as the welding operation, and becomes problematic in other operations performed using the high-luminance/high-illuminance light.

SUMMARY

Provided is a welding information providing apparatus which shows a user welding surrounding environment, as well as a welding spot, so as to improve welding accuracy of the user.

Provided is a welding information providing apparatus capable of quickly and accurately providing real-time welding operation images to a user by adjusting an auto-focus mode according to a work environment.

Provided is a welding information providing apparatus having reducing size and weight to provide a user with convenience of wearing.

Additional aspects will be set forth in part in the description which follows and, in part, will be apparent from the description, or may be learned by practice of the presented embodiments.

According to an embodiment of the present disclosure, a welding information providing apparatus includes a main body provided to be worn by a user, a camera unit attached to an outer side of the main body and including at least one camera obtaining welding image frames with respect to a welding operation, a display unit disposed inside the main body and providing a welding image to the user, and a processor configured to control the display unit to display the welding image generated based on the welding image frames, wherein the camera unit obtains the welding image frame by setting or disabling an auto-focus (AF) function according to an input of the user or pre-set conditions.

The welding image may include a composite image in which information capable of providing a guide for a welding operation to the user is displayed.

The camera unit may further include a camera lens unit that adjusts focus and an image sensor unit on which light has passed through the camera lens unit is incident.

The processor may disable the AF function of the camera unit under a first set condition in which a welding operation is in progress and sets the AF function of the camera unit under a second set condition other than the first set condition.

The welding information providing apparatus may further include a sensor unit disposed outside the main body and detecting information regarding a welding operation, wherein the processor may determine that the first set condition is satisfied when information regarding the welding operation detected through the sensor unit is detected and disable the AF function of the camera unit.

The sensor unit may include an optical sensor that detects an amount of external light, and, when an amount of light detected by the optical sensor is equal to or greater than a pre-set reference value, the processor may determine that the first set condition is satisfied and disable the AF function of the camera unit.

The camera lens unit may include a liquid lens that adjusts a focal length using an electrical signal.

The processor may control the camera unit to disable the AF function of the camera unit and to switch to a manual focus (MF) mode according to an input of the user or pre-set conditions.

The welding information providing apparatus may further include a lens unit disposed on a path along which the welding image provided from the display unit passes, wherein the lens unit may adjust a size of the welding image and guide the welding image to both eyes of the user.

The lens unit may include a liquid lens that adjusts a focal length using an electrical signal.

A distance from eyes of the user to the display unit may be equal to or greater than a focal length of the lens unit.

The welding image may be viewed as a real image within the display unit.

Other aspects, features and advantages of the disclosure will become better understood through the accompanying drawings, the claims and the detailed description.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
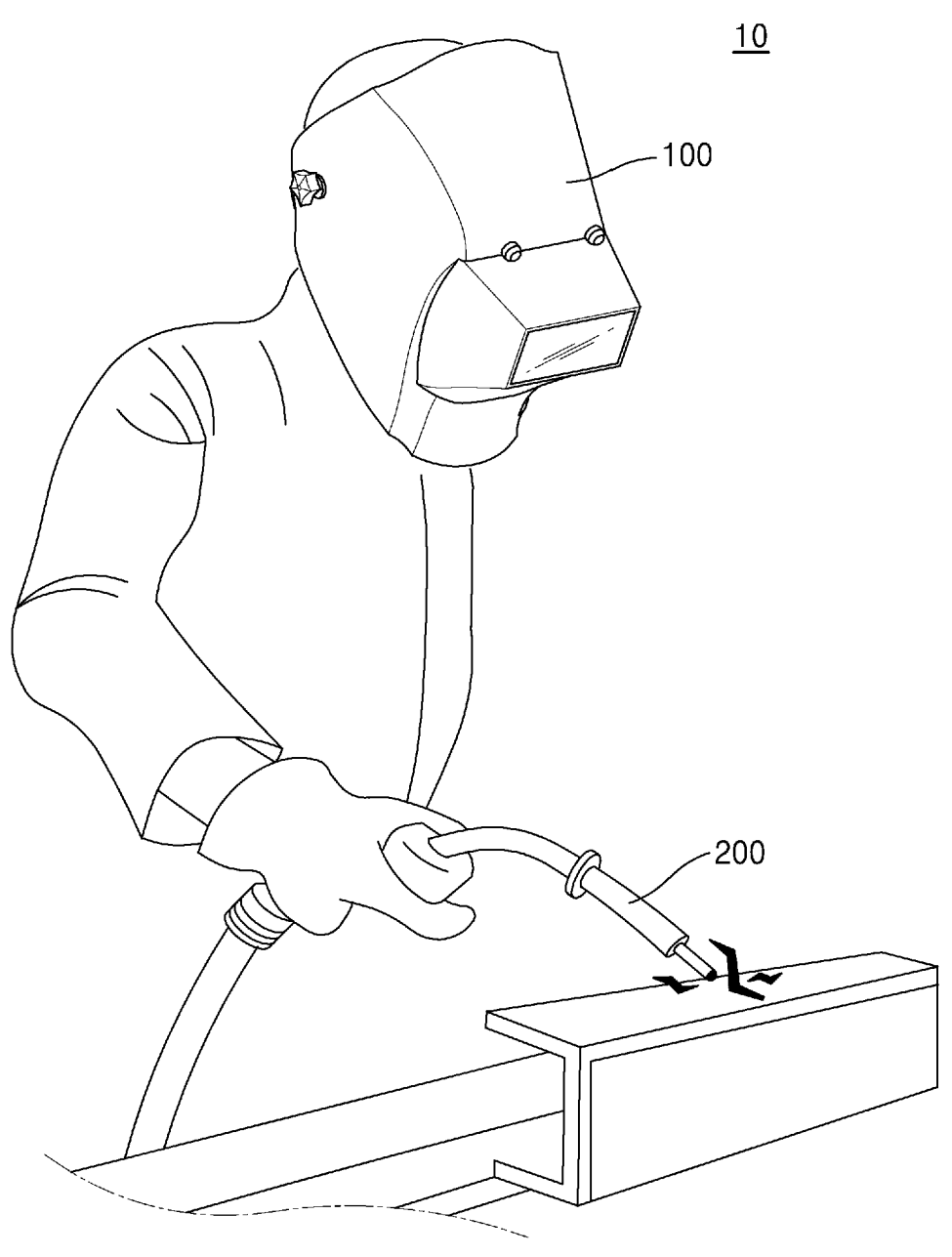
FIG. 1 is a diagram for describing a structure of a welding system according to an embodiment of the present disclosure.

The exemplary embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it can be directly connected or coupled to the other element or intervening elements may be present.

It will be further understood that the terms "comprises," "comprising," "includes" and/or "including," when used herein, specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

FIG. 1 is a diagram for describing a structure of a welding system according to an embodiment of the present disclosure.

Referring to FIG. 1, a welding system 10 according to the present disclosure may include a welding information providing apparatus 100 and a welding torch 200. The welding information providing apparatus 100 and the welding torch 200 may be connected to each other through a communication network to transmit and receive data. The welding information providing apparatus 100 and the welding torch 200 may be matched to each other on an one-to-one basis and operated, but are not limited thereto, and a one-to-n relationship is also available. In other words, n welding torches 200 may be connected to one welding information providing apparatus, or one welding torch 200 may be connected to n welding information providing apparatuses 100. In addition, the welding information providing apparatus 100 and the welding torch 200 may exchange data by communicating with an additional server (not shown).

The welding information providing apparatus 100 may provide information about a welding situation to a user. In detail, the welding information providing apparatus 100 obtains a welding image that is obtained by using at least one camera mounted on the welding information providing apparatus 100, and may generate a composite image based on the welding image and display the image to the user. The welding information providing apparatus 100 may generate the composite image by using a high dynamic range (HDR) technology, and may display a high-definition composite image to the user. Here, the user may visually check information about a shape of welding beads and a surrounding environment other than a portion adjacent to the welding light through the high-definition composite image.

The welding information providing apparatus 100 according to an embodiment of the present disclosure may obtain the welding image by arranging a camera unit at a position equal to the user's field of view. As such, the welding information providing apparatus 100 according to an embodiment of the present disclosure may obtain the welding image that is similar to the view that the user may obtain when directly seeing the working site.

Also, the welding information providing apparatus 100 according to an embodiment of the present disclosure may obtain images from two or more cameras and display the respective images through at least one display in order to provide high-definition composite welding image. For example, the camera unit may include two cameras which may be arranged at positions respectively corresponding to left and right eyes of the user.

The welding information providing apparatus 100 may synthesize images by repeatedly capturing images while varying a shutter speed, an ISO sensitivity, and a gain value of each camera. The welding information providing apparatus 100 according to an embodiment of the present disclosure may improve the image quality by performing a contrast ratio treatment on the composite image.

Also, the welding information providing apparatus 100 of the present disclosure may provide a function of displaying welding information in preferred color (e.g., green and blue) by using RGB. In addition, the welding information providing apparatus 100 of the present disclosure may provide a function of correcting power of a magnifying glass (e.g., screen enlargement and reduction). Also, the welding information providing apparatus 100 of the present disclosure may provide a temperature composite image by using an additional thermal imaging camera. Here, the welding information providing apparatus 100 may indicate a welding temperature in a color. The welding information providing apparatus 100 of the present disclosure may support a function of providing sound (e.g., notification alarm) or guidance voice with respect to the above-described functions.

The welding torch 200 according to an embodiment of the present disclosure may sense a welding situation including a welding temperature, a welding direction, a welding inclination, a welding speed, a distance between a base material and the welding torch, etc. of a real-time welding operation, through at least one sensor. The welding torch 200 may monitor a state of the torch and may change a setting value of a welding torch operation according to the welding situation.

The welding information providing apparatus 100 of the present disclosure may receive information about an operation setting and an operation state from the welding torch 200 through a communication network connected to the welding torch 200, and may provide the user with operation information based on the received welding information through visual feedback.

For example, when receiving sensing information about the welding temperature value, the welding information providing apparatus 100 may output a notification corresponding to the temperature value in various methods, e.g., light, vibration, message, etc. Here, the notification may be visual feedback provided on the display unit or the display, or may be audible feedback provided through sound (e.g., notification alarm) or guiding voice.

In addition, the sensing information about the temperature value may include information about whether the temperature value exceeds a temperature range set in advance, etc. Also, the sensing information about the temperature value may include a numerical value, a grade, a level, etc. corresponding to the temperature value on a welding surface.

When it is determined that the temperature values of the torch and the welding surface exceed the temperature range set in advance, the welding information providing apparatus 100 according to an embodiment of the present disclosure may guide the user to stop the operation. When welding is out of the preset temperature range, the quality of welding may be deteriorated, and thus, the user may be guided to adjust the temperature value of the welding torch 200.

Here, the visual feedback may denote providing of an icon indicating danger on a part of the display unit of the welding information providing apparatus 100, which is displaying the working site. In another example, the welding information providing apparatus 100 may provide an operation suspending guidance through the visual feedback by repeatedly increasing and decreasing a saturation of a certain color (e.g., red) on the entire screen of the display unit.

According to an embodiment of the present disclosure, the welding information providing apparatus 100 may sense the welding information via a sensor included in the welding information providing apparatus 100, in addition to at least one sensor included in the welding torch 200. Here, the welding information including the welding situation, e.g., a degree of light related to the real-time welding operation, a welding temperature, a welding direction, a welding inclination, a welding speed, a distance between the base material and the welding torch, etc. may be sensed via at least one sensor.

Likewise, the welding information providing apparatus 100 may provide guidance corresponding to the welding information based on the welding information sensed by the sensor included in the welding information providing apparatus 100.

According to an embodiment of the present disclosure, the welding information providing apparatus 100 may change a movement of the welding torch 200 by sensing a preset user movement or a preset user voice after the operation suspension guidance is provided.

In another embodiment, when communication between the welding information providing apparatus 100 and the welding torch 200 is not sufficiently performed, the welding information providing apparatus 100 may obtain temperature values of the torch and the welding surface through an image sensing provided therein. For example, the welding information providing apparatus 100 may obtain temperature values of the torch and the welding surface based on image data obtained through a thermal imaging camera.

Although the above example illustrates that information received from the welding torch 200 only includes welding temperature information, the welding information providing apparatus 100 may provide various guidance for various welding information.

Meanwhile, according to an embodiment, the welding information providing apparatus 100 may be connected to an external device (not shown) through a communication network and provide a composite image containing information about a welding situation to a third party. Here, the external device may include an input/output interface. The third party may check the composite image provided from the welding information providing apparatus 100 and monitor the welding situation through an output interface such as a display included in the external device. Also, the third party may input information needed for a worker through the input interface, and the input information may be transmitted to the welding information providing apparatus 100 through a communication network, output in various forms such as visual feedback or auditory feedback, and may be provided to a worker.

Figure 2:
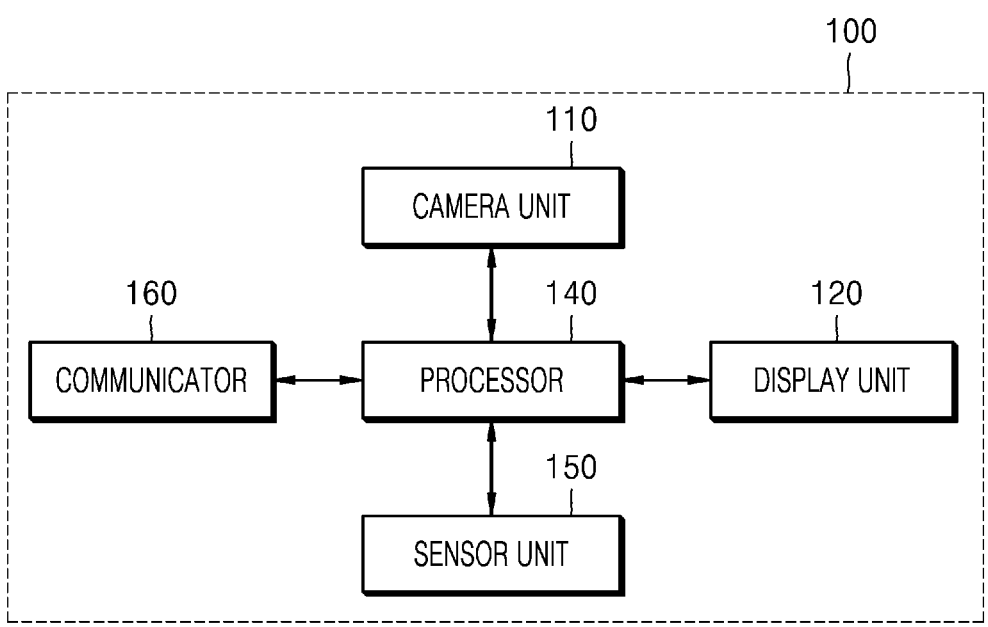
FIG. 2 is a simple block diagram illustrating components of a welding system according to an embodiment of the present disclosure.
Figure 3:
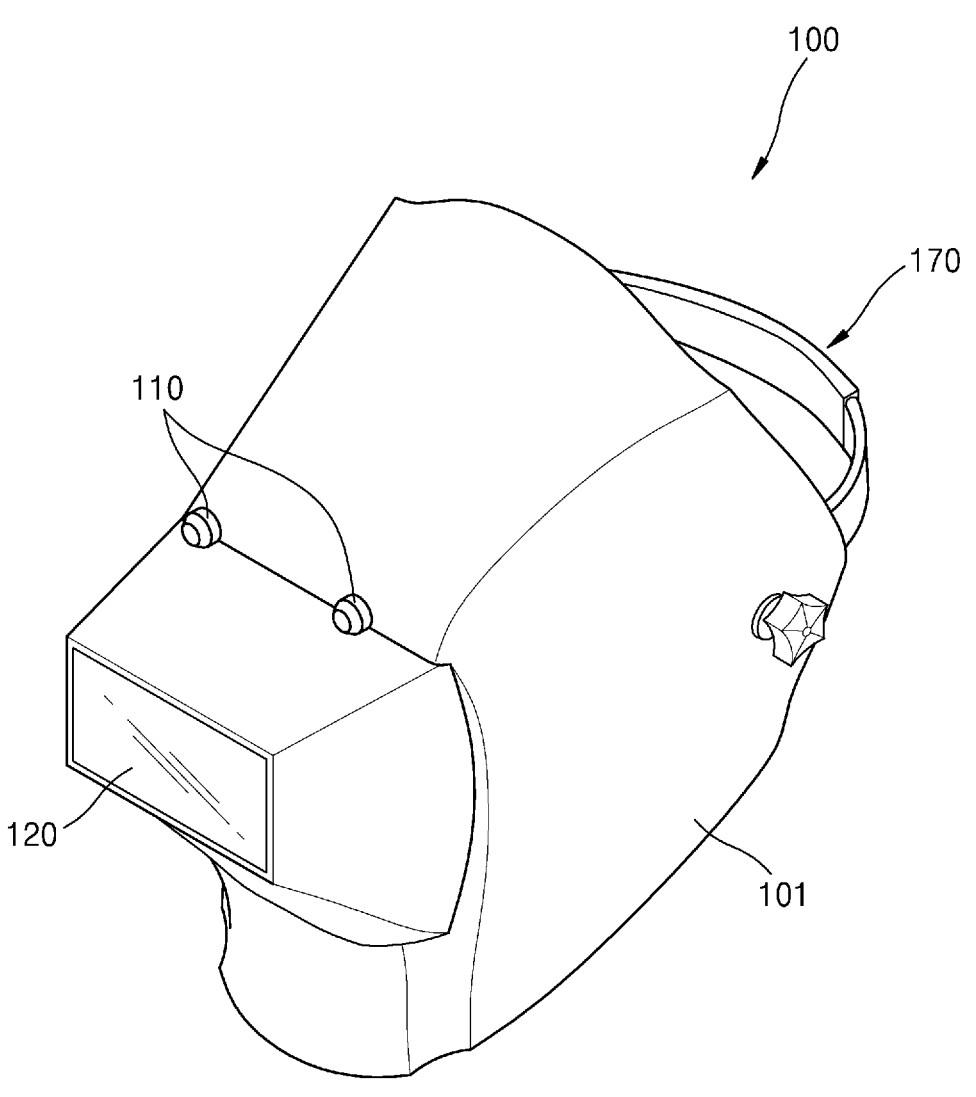
FIG. 3 is a schematic view of a welding information providing apparatus according to another embodiment of the present disclosure.
Figure 4:
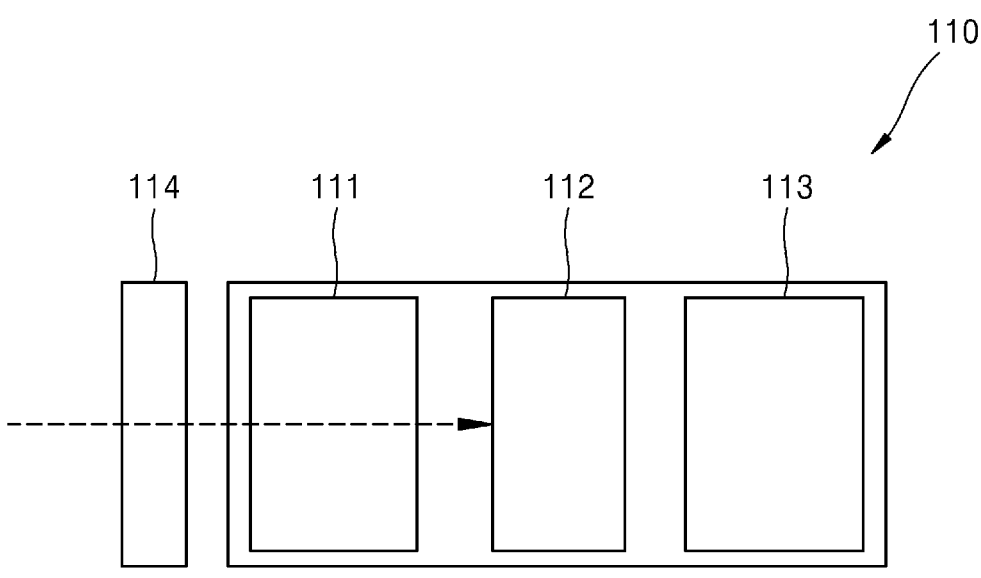
FIG. 4 is a simple block diagram illustrating a camera according to an embodiment of the present disclosure.

FIG. 2 is a simple block diagram illustrating components of a welding system according to an embodiment of the present disclosure, FIG. 3 is a schematic view of a welding information providing apparatus according to another embodiment of the present disclosure, and FIG. 4 is a simple block diagram illustrating a camera according to an embodiment of the present disclosure.

Referring to FIGS. 2 to 4, a welding system 10 may include the welding information providing apparatus 100 and the welding torch 200. The welding information providing apparatus 100 may include a main body 101, a camera unit 110, a display unit 120, a lens unit 130, a processor 140, a sensor unit 150, and a communicator 160.

In addition, the welding information providing apparatus 100 may include an outer cover unit 180 protecting the display unit 120 and a fixing unit 170 disposed on the rear surface of the main body 101 to fix the welding information providing apparatus 100 to a user's head.

The main body 101 is for protecting the user's face and may be provided so as to be worn by the user. The main body 101 may include a material having a predetermined strength, e.g., reinforced plastic, but is not limited thereto, that is, may include various materials having resistance against such elements as sparks that may generate during a welding operation.

The main body 101 may be fixed to the user's head through the fixing unit 170 provided inside the main body 101. The fixing unit 170 may have a structure including a plurality of ribs, such as a headgear, and an element including a soft material such as a fiber material or a cushion material may be disposed on at least a portion of an inner surface in direct contact with the user's head.

The camera unit 110 is mounted on the outside of the main body 101 and may include the at least one camera acquiring the welding image frame for the welding operation. A camera of the camera unit 110 may be disposed on a front portion of a main body 101 to be positioned at a height similar to an user's field of view, and through this, may obtain the same image as at the user's eye level.

The camera unit 110 may include one camera to obtain the welding image frame for the welding operation, but the present disclosure is not limited thereto. As another embodiment, the camera unit 110 may arrange two cameras at positions corresponding to each of the user's left and right eyes. As another embodiment, the camera unit 110 may further include a camera acquiring the welding image frame by photographing at a location other than the front portion of the main body 101 corresponding to the user's field of view.

The camera of the camera unit 110 may receive a control command from the processor 140 and change settings such as shutter speed, ISO sensitivity, gain, and auto focus (AF) in response to the control command to photograph a welding operation.

The camera unit 110 may further include a camera lens unit 111, an image sensor unit 112, and a lens driving unit 113. Light may be incident on the camera unit 110 through the camera lens unit 111 disposed in the direction of the line of sight of a person, and incident light may be converted into an electrical signal by the image sensor unit 112.

The camera lens unit 111 may include at least one lens. The lens of the camera lens unit 111 may be disposed in front of the camera unit 110 (in the direction of the line of sight of a user) and may serve to converge light incident on the camera unit 110.

The camera lens unit 111 may include at least one lens with a fixed focus and may be pre-designed in consideration of the magnification and the angle of view of welding images to be provided to a user. According to another embodiment, the camera lens unit 111 may include at least one lens having a variable focus. A variable focus lens is a lens that changes focus according to a user's input or pre-set conditions, and the focus value may be changed by the lens driving unit 113, which will be described later. The camera lens unit 111 may include both a fixed focus lens and a variable focus lens, but the present disclosure is not limited thereto.

The image sensor unit 112 includes at least one image sensor and may convert an optical signal incident through the camera lens unit 111 into an electrical signal. The image sensor unit 112 is disposed in the optical axis-wise direction of the camera lens unit 111 and may be disposed behind the camera lens unit 111. According to another embodiment, when the camera unit 110 includes a reflective member, the path of light received from the camera lens unit 111 is changed, and the image sensor unit 112 may be positioned on an optical path capable of receiving light.

The lens driving unit 113 may change the focus of the camera lens unit 111 by providing an electric signal to the lens of the camera lens unit 111. According to an embodiment, the lens driving unit 113 may include a motor, a coil, a magnet, an elastic member, etc. to drive the camera lens unit 111. The camera unit 110 may have an auto-focus function that automatically focuses an image on the image sensor unit 112, and the lens driving unit 113 may move the lens of the camera lens unit 111 in a certain direction or changing the focus of the lens to preform auto-focus function.

The lens driving unit 113 may adjust the focus of the camera unit 110 in response to a control command from the processor 140. According to another embodiment, the lens driving unit 113 may be controlled by a separate camera control unit.

The camera unit 110 may be protected by a camera cover unit 114. The camera cover unit 114 may include a light-blocking cartridge, and the light-blocking cartridge may block welding light generated when welding occurs. In other words, the camera unit 110 may capture a welding image in which a certain amount of welding light is blocked by the light-blocking cartridge disposed in front of the camera unit 110.

The light-blocking cartridge may increase a light-blocking degree of the cartridge based on a welding light information detected through the sensor unit 150, for example, a photo sensor. In this case, the light-blocking cartridge may include, for example, a liquid crystal panel (LCD panel) in which a degree of darkening may be adjusted according to the alignment direction of the liquid crystal. For example, the light-blocking cartridge may be implemented with various panels such as vertical align (VA) type LCD, twist nematic (TN) type LCD and in plane switching (IPS) type LCD.

The degree of darkening of the light-blocking cartridge may be adjusted automatically according to the brightness of the welding light. As described above, when automatically adjusted according to the brightness of the welding light, the sensor unit 150 may be used. The sensor unit 150 detects the intensity of the welding light to obtain welding light information, and transmits the information on the intensity of the welding light included in the welding light information as a predetermined electrical signal to the processor 140 to be described later, the processor 140 may control the degree of darkening based on the intensity of the welding light.

In other words, the light-blocking cartridge may change a light-blocking degree of a panel in real time to correspond to intensity of light generated from a welding surface at the welding operation site, and the camera unit 110 may capture a welding image in which a certain amount of welding light is blocked by the light-blocking cartridge. Therefore, the welding information providing apparatus 100 may protect eyes of a user and the sensor(s) of the welding information providing apparatus 100 from strong light generated during a welding operation, obtain a welding image, and provide the welding image to the user.

According to another embodiment of the present disclosure, the welding information providing apparatus 100 may not include the light-blocking cartridge. In this case, the user may perform welding operation only with the welding image obtained via the camera unit 110.

The camera unit 110 according to an embodiment of the present disclosure may include a thermal imaging camera. The welding information providing apparatus 100 may obtain a temperature image by synthesizing a thermal image obtained by thermal imaging camera with an image of a welding site.

The display unit 120 is disposed inside the main body 101 and may provide a welding image to a user. According to an embodiment, the display unit 120 may be disposed on an extension of the line of sight of a user and display a welding image toward eyes of the user.

According to another embodiment, the welding information providing apparatus 100 may further includes a path change member, etc., such that the display unit 120 is disposed inside the main body 101 at a position capable of indirectly providing a welding image through the path change member, etc. rather than a position for directly providing a welding image to eyes of a user.

The display unit 120 may provide a welding image obtained from the camera unit 110 as it is, or may provide a high-definition composite image including welding information.

The display unit 120 may display the high-definition composite image so that the user may visually confirm the surrounding environment (e.g., pre-worked welding bead, etc.) other than the portion adjacent to the welding light. In addition, the display unit 120 may guide the worker with visual feedback (e.g., a welding progress direction) on a welding progress state.

The display unit 120 may be implemented with various display technologies such as liquid crystal display (LCD), organic light emitting diodes (OLED), light-emitting diode (LED), liquid crystal on silicon (LcoS) or digital light processing (DLP).

According to an embodiment, the display unit 120 may include a transparent display. When a welding image is not provided on the display unit 120 (e.g., power off), a user may directly visually check the environment outside the welding information providing apparatus 100 through the transparent display.

The outer cover unit 180 may be disposed on the outer surface of the display unit 120 to protect the display unit 120. The outer cover unit 180 may include an outer cover frame, an outer cover plate, and a light-blocking cartridge.

The outer cover frame may couple the outer cover unit 180 to the main body 101.

The outer cover plate may be disposed in front of the light-blocking cartridge to protect the light-blocking cartridge. The outer cover plate may include a material through which light may pass, for example, a transparent material. The outer cover plate may include a resin material such as polycarbonate or acryl, and may be formed through an injection molding.

The light-blocking cartridge may block the welding light generated during welding, and the transmittance of the light-blocking cartridge may be changed according to conditions. The light-blocking cartridge included in the outer cover unit 180 may include the same material as the light-blocking cartridge included in the camera cover unit 114. Also, the light-blocking cartridge included in the outer cover unit 180 may operate in conjunction with the light-blocking cartridge included in the camera cover unit 114, but the present disclosure is not limited thereto.

According to an embodiment, when a welding operation begins, the light-blocking cartridge included in the camera cover unit 114 may block the welding light to an appropriate level, such that the camera unit 110 may obtain a welding image. In contrast, the light-blocking cartridge included in the outer cover unit 180 may be completely darkened to block external light from entering the main body 101.

The welding information providing apparatus 100 according to an embodiment of the present disclosure may include the lens unit 130 for transferring a welding image provided by the display unit 120 to both eyes of a user at a short distance. The lens unit 130 may be disposed between the display unit 120 and eyes of a user to help the user to secure a viewing area.

The lens unit 130 may include at least one lens, and the at least one lens may have a convex surface to adjust the size of a welding image provided from the display unit 120 and guide the welding image to both eyes of a user.

Also, the lens unit 130 may include a variable focus lens having a variable focus. The variable focus lens of the lens unit 130 may change the focus thereof by receiving an electrical signal from the processor 140.

The lens unit 130 may provide a welding image with the same focal length to both eyes of a user. However, the present disclosure is not limited thereto, and the lens unit 130 may include two lens units respectively corresponding to the left eye and the right eye of a user. In this case, the lens unit 130 may focus a welding image provided from display unit 120 according to the visual acuity of the left eye and the right eye of a user and provide focused welding images to the left eye and the right eye of the user, respectively.

The lens unit 130 may include glass or a plastic. When the lens unit 130 includes a plastic, a transparent resin, etc. may be used. Also, the lens unit 130 may be coated with a filter that blocks light of a certain wavelength band. For example, the lens unit 130 may include a lens coated with a blue light-blocking filter.

The processor 140 may synthesize welding image frames received via the camera unit 110 to generate a high-definition synthesized image. The processor 140 may obtain a synthesized image by setting different photographing conditions of the camera unit 110 for respective frames and synthesizing frames, which are obtained in time order, in parallel. Specifically, the processor 140 may control the camera unit 110 to take pictures by changing the shutter speed, ISO sensitivity, gain, and the auto-focus function of the camera of the camera unit 110.

In this case, the processor 140 may set different shooting conditions according to conditions such as the sensed welding site's welding light, ambient light and the degree of movement of the welding torch 200. Specifically, the processor 140 may set the shooting condition to decrease ISO sensitivity and gain as the welding light and/or ambient light of the welding site increases. In addition, when detecting that the movement and/or work speed of the welding torch 200 is fast, the photographing conditions may be set to increase the shutter speed.

The processor 140 may synthesize images of a preset number of frames in parallel. According to an embodiment of the present disclosure, each image in the preset frame may be captured under different photographing conditions.

When there are two or more cameras of the camera unit 110, the processor 140 according to an embodiment of the present disclosure may control to shoot by differently setting the shooting setting conditions for each camera. Even in this case, the processor 140 may synthesize images of the preset number of frames in parallel.

The processor 140 according to an embodiment of the present disclosure may set the focal length of the camera lens unit 111 of the camera unit 110. The processor 140 may set the focal length of the camera lens unit 111, transmit the focal length to the lens driving unit 113 and control the lens driving unit 113 to change the focal length of the camera lens unit 111.

The processor 140 may set the focal length of the camera lens unit 111 based on light incident on the image sensor unit 112. In detail, the processor 140 may measure the contrast of an image sensed by the image sensor unit 112, determine the difference between a bright portion of the image and a dark portion of the image, and set the focal length. At this time, the processor 140 may control the lens driving unit 113 to find the setting with the highest contrast by moving the lens of the camera lens unit 111 or changing the focus of the lens and set the focal length. However, the present disclosure is not limited thereto. The processor 140 may also set the focal length by using the phase difference of light incident on the image sensor unit 112, and all known auto-focus techniques may be used.

According to another embodiment, the processor 140 may set the focal length of the camera lens unit 111 based on information regarding a welding operation detected through the sensor unit 150. For example, the processor 140 may set the focal length based on light detected through a photo sensor included in the sensor unit 150.

The processor 140 according to an embodiment of the present disclosure may obtain a welding image by setting or disabling the auto-focus (AF) function of the camera unit 110 according to a user's input or pre-set conditions.

When using the auto-focus function, the camera lens unit 111 needs to be adjusted inevitably. Therefore, in a welding image obtained through the camera unit 110, the image may be repeatedly blurred and cleared or be shaken, and a time delay may occur until the focus is set. Furthermore, there is a high possibility that the auto-focus function of the camera unit 110 malfunctions due to the strong light generated during a welding operation.

Therefore, the processor 140 may provide a more accurate welding image to a user by controlling the camera unit 110 to disable the auto-focus function while a welding operation is in progress.

The processor 140 according to an embodiment of the present disclosure may disable the auto-focus function of the camera unit under a first set condition in which a welding operation is being performed and may set the auto-focus function of the camera unit under a second set condition other than the first set condition.

The first set condition may be a condition determined based on information sensed by the image sensor unit 112 or the sensor unit 150 of the camera unit 110 and may be a pre-set condition. The first set condition may be a condition corresponding to a situation in which a welding operation is in progress.

The second set condition is a condition set differently from the first set condition, may be a condition determined based on information sensed by the image sensor unit 112 or the sensor unit 150 of the camera unit 110, and may be a pre-set condition. The second set condition may be a condition corresponding to a situation in which a welding operation is not in progress and may be a condition including all cases that do not correspond to the first set condition. However, the present disclosure is not limited thereto.

According to an embodiment, the sensor unit 150 of the welding information providing apparatus 100 may include an optical sensor that detects the amount of external light. When the amount of light detected by the optical sensor is equal to or greater than a pre-set reference value, the processor 140 may determine that a current situation corresponds to the first set condition and disable the auto-focus function of the camera unit 110. In other words, the welding information providing apparatus 100 may detect strong light generated during a welding operation through an optical sensor, compare detected light with a pre-set value to determine whether the first set condition is satisfied, and disable the auto-focus function of the camera unit 110 based on a result of the determination.

According to another embodiment, the processor 140 may detect the amount of light incident on the image sensor unit 112 and then determine whether the first set condition is satisfied. The processor 140 may compare the amount of light detected by the image sensor unit 112 with a pre-set reference value to determine whether the first set condition is satisfied. The processor 140 may disable the auto-focus function when the first set condition is satisfied (e.g., the amount of light is greater than the reference value) and set the auto-focus function when the second set condition is satisfied e.g., the amount of light is equal to or less than the reference value).

Furthermore, the first set condition may be set to correspond to the measurement values of various sensors, and the welding information providing apparatus 100 may set or disable the auto-focus function of the camera unit 110 by determining whether the first set condition indicating that a user is performing a welding operation is satisfied, by using various sensors.

Also, when disabling the auto-focus function, the processor 140 may calculate the optimal focal length for a welding spot and control the focal length of the camera lens unit 111 to be fixed. In contrast, according to another embodiment, when the auto-focus function of the welding information providing apparatus 100 is disabled, the welding information providing apparatus 100 may be switched to a manual focus mode to allow a user to manually set the optimal focus length.

The processor 140 may control the overall operation of the welding information providing apparatus 100 by using various programs stored in a memory (not illustrated). For example, the processor 140 may include a CPU, a RAM, a ROM and a system bus. Here, the ROM stores a command set for booting a system, and the CPU copies an operating system stored in the memory of the welding information providing apparatus 100 to the RAM according to the commands stored in the ROM and executes the operating system to boot the system. When booting is finished, the CPU may copy various applications stored in the memory to the RAM and execute the applications to perform various operations. In the above description, the processor 140 includes only one CPU, but may include a plurality of CPUs (or DSPs, SoCs, etc.).

According to an embodiment of the present disclosure, the processor 140 may be implemented as a digital signal processor (DSP), a microprocessor, and/or a time controller (TCON) for processing a digital signal. However, one or more embodiments are not limited thereto, and the processor may include one or more from a CPU, a micro controller unit (MCU), a micro processing unit (MPU), a controller, an application processor (AP), a communication processor (CP), and an (advanced RISC machine?) ARM processor, or may be defined by a corresponding term. In addition, the processor 140 may be implemented as a system on chip (SoC) having a built-in processing algorithm, large scale integration (LSI), or a field programmable gate array (FPGA).

An embodiment of the present disclosure may further include a lighting unit (not illustrated) electrically connected to the processor 140. The lighting unit (not illustrated) is located outside the welding information providing apparatus 100 and is configured to irradiate light toward at least a welding operation area. The lighting unit (not illustrated) may include a plurality of LED modules, and the output of light irradiated through the lighting unit (not illustrated) may be adjusted by the processor 140. According to an embodiment, the lighting unit (not illustrated) may operate in conjunction with the operation of the camera unit 110 under the control of the processor 140.

The sensor unit 150 may include a plurality of sensor modules configured to detect various information on the welding site and obtain welding information. Here, the welding information may include a welding temperature, a welding direction, a welding inclination, a welding speed, a distance between the base material and the welding torch from the real-time welding operation. Furthermore, the sensor unit 150 may include an optical sensor module configured to detect a light intensity at least within the welding operation area.

According to an embodiment of the present disclosure, the sensor unit 150 may include an illuminance sensor, and in this case, the sensor unit 150 may obtain information on the welding light intensity of the welding site. In addition to the illuminance sensor, the sensor unit 150 may further include various types of sensors such as a proximity sensor, a noise sensor, a video sensor, an ultrasonic sensor and an RF sensor. and may detect various changes related to a welding operation environment.

The communicator 190 is a component for receiving welding information from the welding torch 200 and transmitting a command for controlling the welding torch 200. According to an embodiment of the present disclosure, the communicator 160 may transmit a synthesized image to an external device in addition to the welding torch 200. Here, the external device may include various devices including a communication module, such as a smart phone of an operator/third party, a computer, etc.

The communicator 160 may be configured to communicate with various types of external devices according to various types of communication methods. The communicator 160 may include at least one of a Wi-Fi chip, a Bluetooth chip, a wireless communication chip, and an NFC chip. In particular, when a Wi-Fi chip or a Bluetooth chip is used, various connection information such as an SSID, a session key, etc. is transmitted/received first, and then, communication is connected using the above connection information and various information may be transmitted/received. The wireless communication chip refers to a chip that performs communication according to various communication standards such as IEEE, Zigbee, 3rd Generation (3G), 3rd Generation Partnership Project (3GPP), Long Term Evolution (LTE), etc. The NFC chip refers to a chip operating in an NFC type using a frequency band of 13.56 MHz from among various RF-ID frequency bands such as 135 kHz, 13.56 MHz, 433 MHZ, 860 to 960 MHz, 2.45 GHz, etc.

Although not shown in the drawings, the welding torch 200 may include a communication unit, a sensor unit, and a second processor.

The communicator 160 transmits and receives data to/from the welding information providing apparatus 100. The communicator includes a module capable of short-range wireless communication (e.g., Bluetooth, Wifi, Wifi-Direct) or long-distance wireless communication (3G, High-Speed Downlink Packet Access (HSDPA) or LTE).

The sensor unit or the second sensor is included in the welding torch and is configured to sense welding conditions such as a welding temperature, a welding speed, a welding inclination, a welding direction, and a distance between the base material and the welding torch.

The sensor unit detects at least one of various changes such as a change in posture of a user holding the welding torch 200, a change in illuminance of the welding surface, a change in an acceleration of the welding torch 200, etc., and may transmit an electrical signal corresponding to the change to the second processor. That is, the sensor unit may sense a state change made based on the welding torch, generate a sensing signal corresponding thereto, and transmit the sensing signal to the second processor.

In the present disclosure, the sensor unit may include various sensors, and when the welding torch 200 is driven (or based on a user setting), power is supplied to at least one sensor that is preset according to control to sense a change in the status of the welding torch 200.

In this case, the sensor unit may be configured to include at least one of all types of sensing devices capable of detecting a change in the status of the welding torch 200. For example, the sensor unit may include at least one of various sensing devices such as an acceleration sensor, a gyro sensor, an illuminance sensor, a proximity sensor, a pressure sensor, a noise sensor, a video sensor, a gravity sensor, etc. The degree of light within the welding operation area sensed by the illuminance sensor of the welding torch 200 may be transferred to the processor 140 via the communication unit, and the processor 140 may control the lighting unit (not shown) and/or the camera unit 110 based on the degree of light transferred through the illuminance sensor of the welding torch 200, not via the sensor unit 150 of the welding information providing apparatus 100.

Meanwhile, the acceleration sensor is a component for sensing movement of the welding torch 200. In detail, the acceleration sensor may measure dynamic forces such as acceleration, vibration, and impact of the welding torch 200, and thus may measure the movement of the welding torch 200.

The gravity sensor is an element for sensing a direction of gravity. In other words, the result of detection by the gravity sensor may be used together with the acceleration sensor to determine the movement of the welding torch 200. In addition, a direction in which the welding torch 200 is gripped may be determined via the gravity sensor.

In addition to the above-described types of sensors, the welding torch 200 may further include various types of sensors such as a gyroscope sensor, a geomagnetic sensor, an ultrasonic sensor, and an RF sensor, and may detect various changes regarding the welding operation environment.

Figure 5:
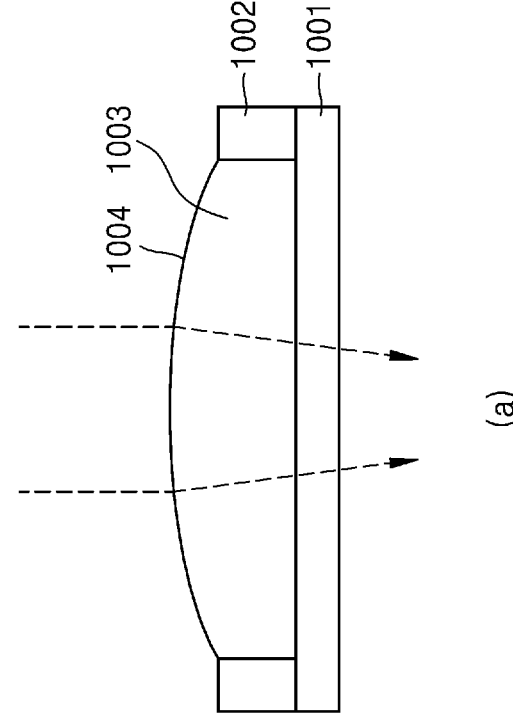
FIG. 5 is a diagram illustrating a liquid lens according to an embodiment of the present disclosure.

FIG. 5 is a diagram illustrating a liquid lens according to an embodiment of the present disclosure.

Referring to FIG. 5, the camera unit 110 or the lens unit 130 according to an embodiment of the present disclosure may include a liquid lens with a variable focal length. The liquid lens may include a plate 1001, a partition wall 1002, and a liquid lens unit 1003.

The plate 1001 or the partition wall 1002 may include at least one substrate that supplies voltage to the liquid lens. Also, the plate 1001 and the partition wall 1002 constitute a cavity into which the liquid lens unit 1003 may be inserted, may serve as a holder to support the liquid lens unit 1003, and portions of the plate 1001 and the partition wall 1002 may constitute a contact area connected to the liquid lens unit 1003.

The liquid lens unit 1003 includes a liquid in at least a portion thereof, and the liquid may include a conductive liquid. Therefore, the curvature of the liquid lens unit 1003 may be changed according to the voltage, allowing the focal length thereof to be adjusted. The edge portion of the liquid lens unit 1003 may be thinner than the center portion of the liquid lens unit 1003.

The liquid lens unit 1003 may include both a conductive liquid and a non-conductive liquid, and the conductive liquid and the non-conductive liquid may form an interface therebetween without being mixed with each other. In this case, the interface between the conductive liquid and the non-conductive liquid may be deformed by the voltage applied to the liquid lens, and thus the focal length may be changed.

By controlling the curvature change or the boundary deformation of the liquid lens according to the voltage, the focal length of the liquid lens may be controlled, and the auto-focus function of the camera unit 110 including the liquid lens may be performed.

The welding information providing apparatus 100 according to an embodiment may include a liquid lens in the camera unit 110 or the lens unit 130, thereby reducing the number of lenses used therein, reducing the volume of the lens driving unit 113 for a focusing function, and reducing power consumption for the focusing function.

Figure 6:
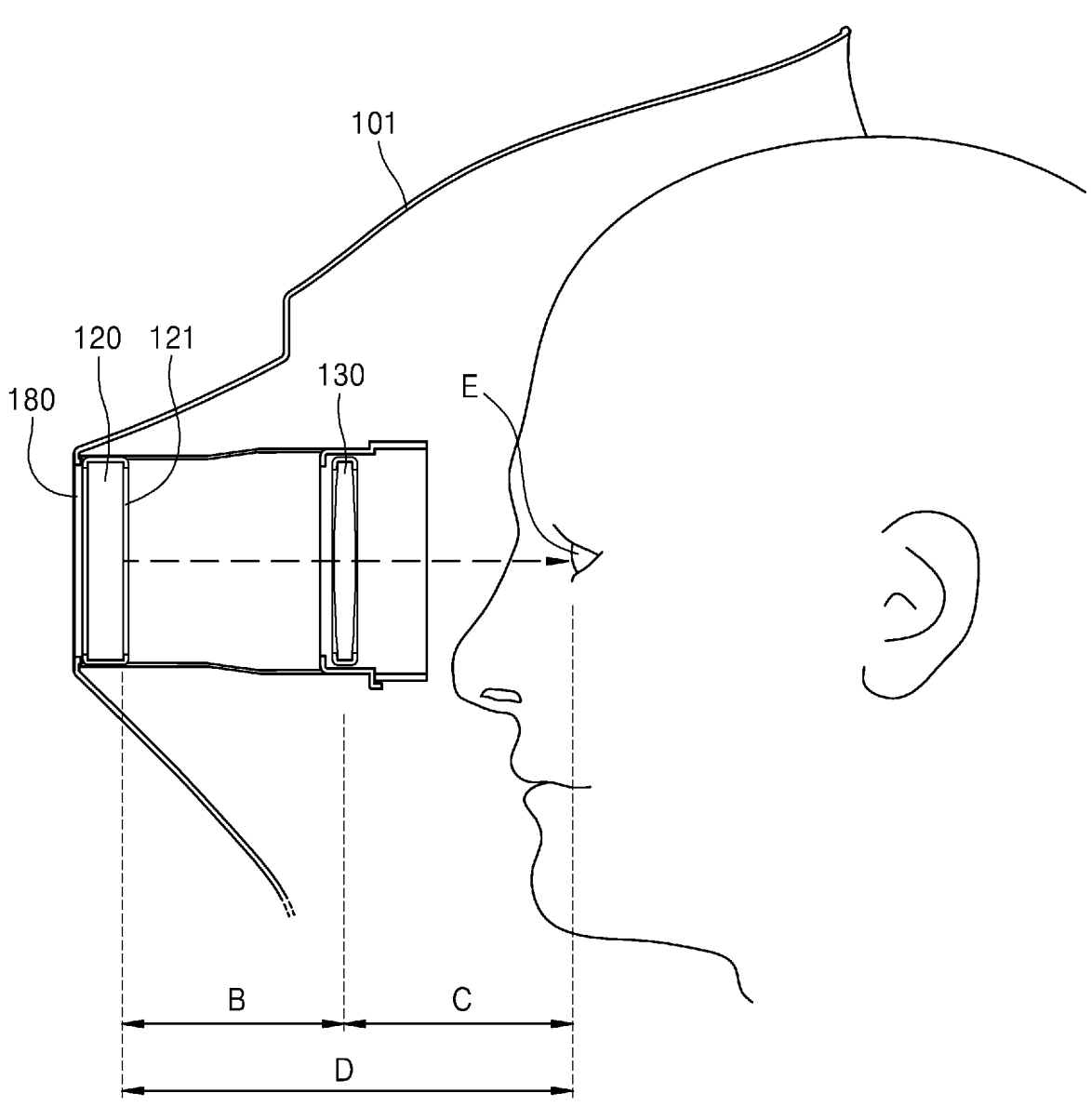
FIG. 6 is a diagram illustrating positions of a display unit and a lens unit of a welding information providing apparatus according to an embodiment of the present disclosure.
Figure 7:
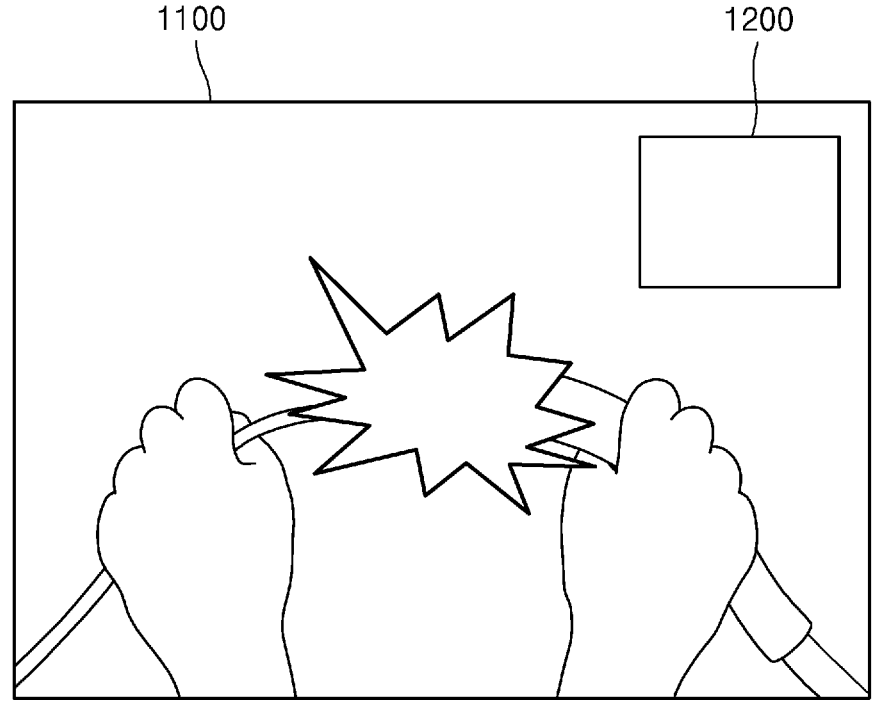
FIG. 7 is a diagram illustrating a composite image according to an embodiment of the present disclosure.

FIG. 6 is a diagram illustrating positions of a display unit and a lens unit of a welding information providing apparatus according to an embodiment of the present disclosure, and FIG. 7 is a diagram illustrating a composite image according to an embodiment of the present disclosure.

Referring to FIGS. 6 and 7, the welding information providing apparatus 100 according to an embodiment of the present disclosure may display a composite welding image 1100 on the display unit 120, and the composite welding image 1100 provided from the display unit 120 may pass through the lens unit 130 and be provided to eyes of a user.

A distance D from eyes of a user to the display unit 120 may be equal to or greater than the focal length of the lens unit 130. The lens unit 130 is arranged to be spaced apart from eyes of a user by a distance C and serves to guide a welding image provided from the display unit 120 to the eyes of the user. At this time, the lens unit 130 may adjust the focal length to form an image on the eyes of the user, and a focal length B formed at this time may correspond to the distance from the lens unit 130 to a screen 121 of the display unit 120. Therefore, a welding image provided to the eyes of the user may be viewed as a real image within the display unit 120, and thus the user may clearly see an image of the display unit 120 provided at a relatively short distance.

According to an embodiment, the display unit 120 may include two display units respectively provided for the left eye and the right eye of the user and may provide different welding images for the left eye and the right eye of the user, respectively. In this case, the welding information providing apparatus 100 may create parallax in a composite image provided to each eye of a user and provide a sense of depth in a welding image provided on a 2-dimensional plane, thereby providing a welding image that is more similar to an actual welding environment and is more stereoscopic to the user.

Also, high-quality composite images may be provided to a user by synthesizing welding image frames captured under various shooting conditions using a HDR method. Through high-definition composite images, a user may easily identify surrounding areas other than an area adjacent to a welding spot (i.e., an overwhelmingly bright area).

The composite welding image 1100 provided through the display unit 120 may be an image in which information 1200 that may provide a guide for a welding operation to a user is displayed on a portion of the display unit 120. Since a user may check a welding operation situation through an image through the camera unit 110 while a welding operation is in progress, a UI providing information about the welding operation situation may be displayed on a welding image, thereby providing a guide to the welding operation to the user. Therefore, the user may check a welding operation in real time and visually check welding information at the same time. The method of displaying a UI that provides welding information to a user is not limited to that shown, and the location, the size, the display time, etc. of the UI may be modified in various ways.

Figure 8:
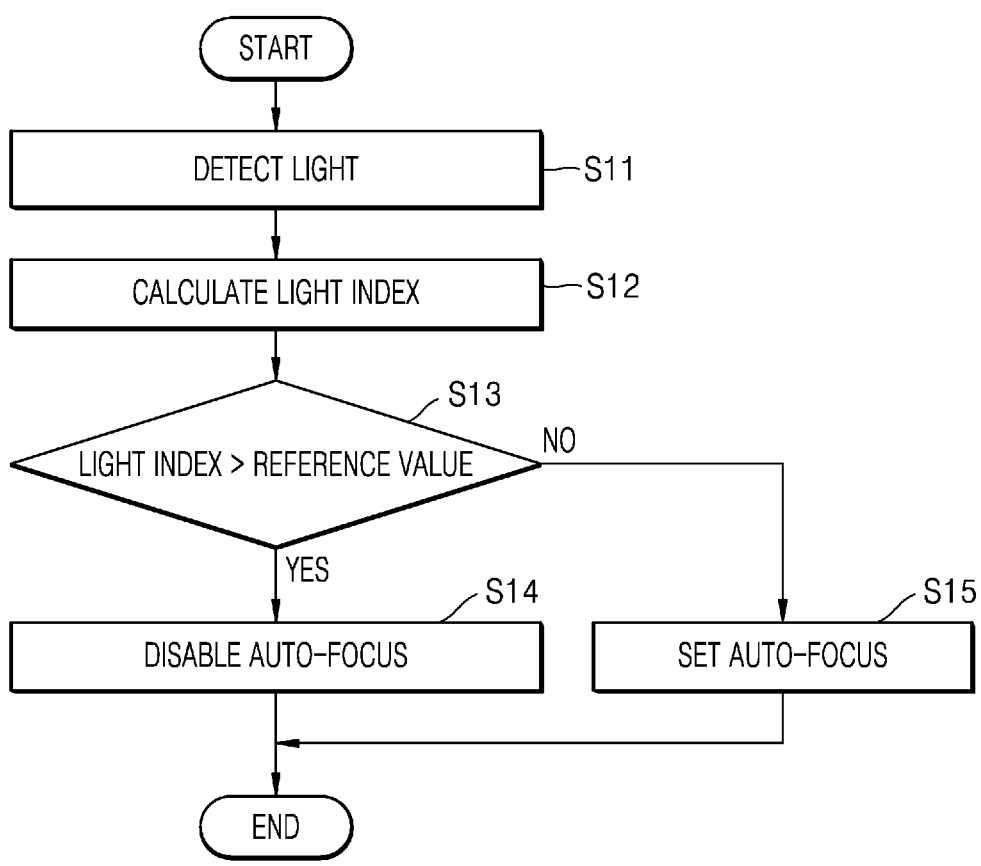
FIG. 8 is a flowchart illustrating an operation process for controlling the focus of a camera unit of a welding information providing apparatus.

FIG. 8 is a flowchart illustrating an operation process for controlling the focus of a camera unit of a welding information providing apparatus, according to an embodiment.

In the welding information providing apparatus 100 according to an embodiment, the processor 140 or a separate camera control unit may control the auto-focus function. Hereinafter, the description will be given under the assumption that the processor 140 controls the auto-focus function.

Referring to FIG. 8, the processor 140 may detect the level of light within a welding operation area by using the camera unit 110 or the sensor unit 150 (operation S11). For example, the welding information providing apparatus 100 may include an illuminance sensor module, and thus the level of light may correspond to data regarding illuminance within the welding operation area. According to another embodiment, the processor 140 may detect the level of light by using a sensor unit included in the welding torch 200.

When data regarding the level of light is transmitted to the processor 140, the processor 140 calculates a light index within the welding operation area based on the data (operation S12). At this time, the welding operation area may be an area including a portion where welding is performed by the welding torch 200. Here, the light index may correspond to data generated by converting the data regarding the level of light to compare with a specific reference value.

Next, the processor 140 compares the light index with a pre-set reference value (operation S13). The reference value may correspond to the illuminance value of light generated at a welding spot as welding begins. The illuminance value of light generated from a welding spot may vary depending on the type or state of welding, and the above-stated reference value may be a value corresponding to the lowest illuminance value. However, the present disclosure is not necessarily limited thereto, and the reference value may include a plurality of values to correspond to types or states of welding.

When the light index is compared with the reference value and the light index is greater than the reference value, the processor 140 disables an auto-focus mode (operation S14) and provides a welding image, which is generated based on welding image frames obtained through the camera unit 110, to a user by displaying the welding image on the display unit 120. As such, when the light index is greater than the reference value, it indicates that welding has begun. Therefore, the processor 140 may disable the auto-focus mode of the camera unit 110 to obtain a welding image based on a manual focus mode or a fixed focus value, thereby providing an accurate welding images without shaking to a user.

The auto-focus mode of the camera unit 110 may be disabled in conjunction with adjustment of the light-blocking cartridge included in the camera cover unit 114. In other words, when a welding operation begins, the camera unit 110 may obtain a welding image by blocking a significant amount of welding light and obtain a welding image with a fixed focus value.

Meanwhile, when the light index is less than or equal to the reference value, it is determined that a welding operation is not being performed, and thus the processor 140 may control the camera unit 110 to obtain an image in the auto-focus mode (operation S15). When a user stops a welding operation in progress and the line of sight of the user is at the surrounding environment away from a welding spot, the welding information providing apparatus 100 may provide a clear image with adjusted focal length to the user by using an auto-focus mode.

As described above, a welding information providing apparatus according to embodiments of the present disclosure may use a liquid lens in a camera unit or a lens unit, thereby reducing the volume and the weight of the same and providing convenience for wearing to a user. Also, a welding information providing apparatus according to embodiments of the present disclosure may provide, to a user, an image that is more accurate and clearer by setting or disabling an auto-focus mode according to work situations.

A welding information providing apparatus according to embodiments of the present disclosure may be used for training for workers. According to an embodiment, a welding information providing apparatus may provide a composite image containing information regarding a welding situation to a user and, at the same time, provide the composite image to an external device connected to the welding information providing apparatus through a communication network. A third party may check the composite image by using a display included in the external device and monitor the welding situation of the user. Also, a third party may additionally input information needed by the user using an input interface included in the external device. The user may check additional information entered by the third party through the welding information providing apparatus.

According to another embodiment, a welding information providing apparatus may provide a composite image containing information regarding a welding situation to an external server connected to the welding information providing apparatus through a communication network. The external server may include a learning model trained by using various welding images, may receive a composite image provided from the welding information providing apparatus, and output necessary information for a welding operation. The necessary information output from the external server may be provided to the user through the welding information providing apparatus.

Meanwhile, in the present specification, descriptions have been given based on an embodiment in which a welding information providing apparatus is used in a welding operation to provides a welding image. However, the present disclosure is not limited thereto, and the present disclosure may be applied to skin treatment and/or diagnosis using high-brightness/high-illuminance light and may also be applied to operations of other fields using high-brightness/high-illuminance light. Also, the present disclosure may be applied to education in operations of fields using high-brightness/high-illuminance light.

A welding information providing apparatus according to embodiments of the present disclosure may provide a more accurate welding image to a user by setting or disabling an auto-focus function of a camera unit that obtains a welding image according to the work environment.

Also, a welding information providing apparatus according to embodiments of the present disclosure may use a lens with variable focal length, thereby reducing the number and/or the size of lenses used therein and configuring the size of a main body to be compact.

Also, the welding information providing apparatus may provide efficient guidance to a user by displaying a current welding operation status of the user on a welding image, and thus the user may obtain optimal visual information and improve welding quality.

It may be obvious that the scope of the present disclosure is not limited by these effects.

While the disclosure has been particularly shown and described with reference to exemplary embodiments thereof, it will be understood by those of ordinary skill in the art that various changes in form and details may be made therein without departing from the spirit and scope as defined by the following claims. Therefore, the scope sought to be protected of the disclosure shall be defined by the appended claims.

What is claimed is:

1. A welding information providing apparatus comprising:
a main body provided to be worn by a user;
a camera unit attached to an outer side of the main body and comprising at least one camera obtaining welding image frames with respect to a welding operation;
a display unit disposed inside the main body and providing a welding image to the user;
a processor configured to control the display unit to display the welding image generated based on the welding image frames, and
a sensor unit disposed outside the main body and detecting information regarding a welding operation,
wherein the camera unit obtains the welding image frames by setting or disabling an auto-focus (AF) function according to an input of the user or pre-set conditions,
wherein the processor disables the AF function of the camera unit under a first set condition in which a welding operation is in progress and sets the AF function of the camera unit under a second set condition other than the first set condition,
wherein the processor determines that the first set condition is satisfied when information regarding the welding operation detected through the sensor unit is detected and disables the AF function of the camera unit,
wherein the sensor unit comprises an optical sensor that detects an amount of external light, and, when an amount of light detected by the optical sensor is equal to or greater than a pre-set reference value, the processor determines that the first set condition is satisfied and disables the AF function of the camera unit.

2. The welding information providing apparatus of claim 1, wherein the welding image comprises a composite image in which information capable of providing a guide for a welding operation to the user is displayed.

3. The welding information providing apparatus of claim 1, wherein the camera unit further comprises a camera lens unit that adjusts focus and an image sensor unit on which light has passed through the camera lens unit is incident.

4. The welding information providing apparatus of claim 3, wherein the camera lens unit comprises a liquid lens that adjusts a focal length using an electrical signal.

5. The welding information providing apparatus of claim 1, wherein the processor is configured to control the camera unit to disable the AF function of the camera unit and to switch to a manual focus (MF) mode according to an input of the user or pre-set conditions.

6. The welding information providing apparatus of claim 1, further comprising a lens unit disposed on a path along which the welding image provided from the display unit passes,
wherein the lens unit adjusts a size of the welding image and guides the welding image to both eyes of the user.

7. The welding image providing apparatus of claim 6, wherein the lens unit comprises a liquid lens that adjusts a focal length using an electrical signal.

8. The welding image providing apparatus of claim 6, wherein a distance from eyes of the user to the display unit is equal to or greater than a focal length of the lens unit.

9. The welding information providing apparatus of claim 1, wherein the welding image is viewed as a real image within the display unit.

10. A welding information providing apparatus comprising:

a main body provided to be worn by a user;

a camera unit attached to an outer side of the main body and comprising at least one camera obtaining welding image frames with respect to a welding operation;

a sensor unit disposed outside the main body and detecting information regarding a welding operation; and a processor electrically connected to the camera unit and the sensor unit, wherein the camera unit obtains the welding image frames by setting or disabling an auto-focus (AF) function according to an input of the user or pre-set conditions, the processor disables the AF function of the camera unit under a first set condition in which a welding operation is in progress and sets the AF function of the camera unit under a second set condition other than the first set condition, and the sensor unit detects an amount of external light, and, when an amount of light detected by the optical sensor is equal to or greater than a pre-set reference value, the processor determines that the first set condition is satisfied and disables the AF function of the camera unit.

11. The welding information providing apparatus of claim 10, wherein the camera unit further comprises a camera lens unit that adjusts focus and an image sensor unit on which light has passed through the camera lens unit is incident.

12. The welding information providing apparatus of claim 11, wherein the camera lens unit comprises a liquid lens that adjusts a focal length using an electrical signal.

13. The welding information providing apparatus of claim 10, wherein the processor is configured to control the camera unit to disable the AF function of the camera unit and to switch to a manual focus (MF) mode according to an input of the user or pre-set conditions.

14. The welding information providing apparatus of claim 10, further comprising a lens unit disposed on a path along which the welding image provided from the display unit passes, wherein the lens unit adjusts a size of the welding image and guides the welding image to both eyes of the user.

15. The welding information providing apparatus of claim 14, wherein the lens unit comprises a liquid lens that adjusts a focal length using an electrical signal.

16. The welding information providing apparatus of claim 14, wherein a distance from eyes of the user to the display unit is equal to or greater than a focal length of the lens unit.

17. The welding information providing apparatus of claim 10, wherein the welding image is viewed as a real image within the display unit.

* * * * *